United States Patent
Shanbhag et al.

(10) Patent No.: US 10,436,858 B2
(45) Date of Patent: Oct. 8, 2019

(54) METHOD AND SYSTEM FOR IMPROVED CLASSIFICATION OF CONSTITUENT MATERIALS

(71) Applicant: General Electric Company, Schenectady, NY (US)

(72) Inventors: Dattesh Dayanand Shanbhag, Bangalore (IN); Rakesh Mullick, Bangalore (IN); Sheshadri Thiruvenkadam, Bangalore (IN); Florian Wiesinger, Garching (DE); Sudhanya Chatterjee, Bangalore (IN); Kevin Matthew Koch, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 140 days.

(21) Appl. No.: 15/532,680

(22) PCT Filed: Dec. 2, 2015

(86) PCT No.: PCT/US2015/063392
§ 371 (c)(1),
(2) Date: Jun. 2, 2017

(87) PCT Pub. No.: WO2016/089976
PCT Pub. Date: Jun. 9, 2016

(65) Prior Publication Data
US 2017/0371010 A1    Dec. 28, 2017

(30) Foreign Application Priority Data
Dec. 4, 2014   (IN) .......................... 6113/CHE/2014

(51) Int. Cl.
*G01R 33/565* (2006.01)
*G01R 33/24* (2006.01)
*A61B 5/055* (2006.01)
*A61B 5/00* (2006.01)
*G01R 33/56* (2006.01)
*G01R 33/48* (2006.01)

(52) U.S. Cl.
CPC .......... *G01R 33/243* (2013.01); *A61B 5/0035* (2013.01); *A61B 5/055* (2013.01);
(Continued)

(58) Field of Classification Search
CPC ...... A61B 5/0035; A61B 5/05; G01R 33/243; G01R 33/481; G01R 33/4816; G01R 33/5608; G01R 33/56563; G01R 33/56536
(Continued)

(56) References Cited

U.S. PATENT DOCUMENTS 5,351,006 A    9/1994  Sumanaweera et al.
6,477,398 B1 *  11/2002  Mills .................. G01R 33/16
                                                              324/201

(Continued)

FOREIGN PATENT DOCUMENTS

WO    2014190115 A1    11/2014

OTHER PUBLICATIONS

International Search Report and Written Opinion for International Application No. PCT/US2015/063392 dated Mar. 14, 2016. 11 pages.

*Primary Examiner* — Patrick Assouad
*Assistant Examiner* — Demetrius R Pretlow (57) ABSTRACT

An imaging system and method are disclosed. An MR image and measured B0 field map of a target volume in a subject are reconstructed, where the MR image includes one or more bright and/or dark regions. One or more distinctive constituent materials corresponding to the bright regions are identified. Each dark region is iteratively labeled as one or more ambiguous constituent materials. Susceptibility values corresponding to each distinctive and iteratively labeled ambiguous constituent material is assigned. A simulated B0 field map is iteratively generated based on the assigned (Continued)

susceptibility values. A similarity metric is determined between the measured and simulated B0 field maps. Constituent materials are identified in the dark regions based on the similarity metric to ascertain corresponding susceptibility values. The MRI data is corrected based on the assigned and ascertained susceptibility values. A diagnostic assessment of the target volume is determined based on the corrected MRI data.

19 Claims, 5 Drawing Sheets

(52) U.S. Cl.
CPC ........ *G01R 33/5608* (2013.01); *G01R 33/481* (2013.01); *G01R 33/4816* (2013.01); *G01R 33/56536* (2013.01)

(58) Field of Classification Search
USPC ......................................................... 324/307
See application file for complete search history.

(56) References Cited

U.S. PATENT DOCUMENTS

| 8,731,256 | B2* | 5/2014 | Mori | ...................... G01R 33/56 |
| | | | | 382/128 |
| 2001/0029329 | A1* | 10/2001 | Avrin | .................. A61B 5/04005 |
| | | | | 600/407 |
| 2004/0032261 | A1 | 2/2004 | Schweikard et al. | |
| 2004/0254449 | A1* | 12/2004 | Roopchansingh | ........................ |
| | | | | G01R 33/56563 |
| | | | | 600/410 |
| 2009/0256567 | A1* | 10/2009 | Aksit | .................... G01R 33/243 |
| | | | | 324/312 |
| 2011/0044524 | A1* | 2/2011 | Wang | ..................... G01R 33/54 |
| | | | | 382/131 |
| 2011/0262021 | A1 | 10/2011 | Liu | |
| 2012/0141003 | A1* | 6/2012 | Wang | ..................... G01R 33/24 |
| | | | | 382/131 |
| 2013/0102879 | A1 | 4/2013 | MacLaren et al. | |
| 2014/0062475 | A1* | 3/2014 | Koch | ........... G01R 33/56563 |
| | | | | 324/309 |
| 2014/0225610 | A1* | 8/2014 | Popescu | ........... G01R 33/56563 |
| | | | | 324/309 |
| 2014/0296702 | A1* | 10/2014 | Griswold | ........... G01R 33/3614 |
| | | | | 600/416 |
| 2015/0051475 | A1* | 2/2015 | Leussler | ............ G01R 33/4804 |
| | | | | 600/411 |
| 2015/0160321 | A1* | 6/2015 | Patil | ................. G01R 33/56563 |
| | | | | 324/309 |
| 2015/0168525 | A1* | 6/2015 | Sato | ................... G01R 33/5608 |
| | | | | 324/318 |

* cited by examiner

METHOD AND SYSTEM FOR IMPROVED CLASSIFICATION OF CONSTITUENT MATERIALS

CROSS-REFERENCE TO RELATED APPLICATIONS

This is a national stage application under 35 U.S.C. § 371 (c) of PCT Patent Application No. PCT/US2015/063392, filed on Dec. 2, 2015, which claims priority to India Patent Application No. 6113/CHE/2014, filed on Dec. 4, 2014, the disclosures of which are incorporated herein by reference in their entireties.

BACKGROUND

Embodiments of the present specification relate generally to diagnostic imaging, and more particularly to methods and systems for improved classification of constituent materials in a magnetic resonance (MR) image.

Magnetic resonance imaging (MRI) provides high-quality images with excellent soft-tissue contrast for use in diagnosis and/or treatment of a patient. Particularly, MRI may be used in conjunction with one or more other imaging modalities to provide complementary diagnostic information for use in studying biochemical processes in greater detail. For example, MRI may be used to complement molecular information offered by a positron emission tomography (PET) system for tracking biomarkers with higher sensitivity.

Typically, PET imaging entails photon-electron interactions that may result in attenuation of emitted photons, which in turn, leads to degraded image quality and inaccurate PET quantitation. Use of MRI data aids in correction of PET attenuation values, thus providing more accurate clinical information. Particularly, the PET attenuation values may be corrected using MRI data that is accurately classified into corresponding constituent materials, such as specific tissues, air, fat, water, bone, metal, and/or other materials.

Conventional MRI generates positive response signals having different signal intensities or brightness for portions of an imaged region that includes soft tissues, water, and/or fat. For example, response signals received from liver tissues may have a particular signal intensity that is different from a signal intensity of response signals received from stomach tissues. A difference in signal intensities, thus, may be used to distinctly classify constituent materials in the imaged region.

However, conventional MRI fails to generate response signals having such distinctive signal intensities when imaging regions that are devoid of water or fat molecules. For example, conventional MRI pulse sequences generate indistinct dark signals when imaging regions including air, bone, and/or metal even though these constituent materials have substantially different attenuation values. Moreover, MRI of regions proximal to metal objects such as pacemakers or dental fillings may cause excessive heating and/or image artifacts due to large susceptibility variations between metal and surrounding tissue. Specifically, presence of metals in an imaged region may cause significant resonant frequency changes during MRI, thereby resulting in substantial signal loss, failure of fat suppression, geometric distortion, and bright pile-up artifacts.

Accordingly, certain conventional MRI systems provide classification methods that attempt to differentiate regions including air from bone structures and metal based on differences in signal intensity, relaxivity, chemical shifts, and/or image gradient information. Certain other classification methods entail magnetic field mapping around metal implants using an asymmetric spin-echo MRI sequence, ultra-short echo-time (UTE) and/or zero-echo time (ZTE) MRI pulse sequences to resolve ambiguity between different constituent materials.

However, even such conventional classification methods fail to mitigate inaccuracies in determined diagnostic information resulting from large signal losses caused by presence of metal objects in the imaged region. Specifically, magnetic susceptibility artifacts that arise due to presence of metal, for example, in the dental fillings or in hip-joint implants distort the diagnostic information derived from MR images. The distorted MR image information fails to aid in accurate and efficient classification of imaged regions in and/or near air, bones and/or metal. The inefficient classification, in turn, precludes use of the MR image information for accurate estimation of PET attenuation values and/or any other biochemical investigation. Magnetic susceptibility artifacts, thus, render conventional MRI unsuitable for a variety of clinical applications.

BRIEF DESCRIPTION

In accordance with certain aspects of the present specification, a method for imaging a subject is presented. The method includes reconstructing an MR image and a measured B0 field map corresponding to a target volume in a subject using MRI data acquired from the target volume, where the MR image includes one or more bright regions and/or one or more dark regions. Further, the method includes identifying one or more distinctive constituent materials corresponding to each of the one or more bright regions in the MR image. Moreover, the method includes iteratively labeling each of the one or more dark regions in the MR image as one or more ambiguous constituent materials. Additionally, the method includes assigning susceptibility values corresponding to each of the one or more distinctive constituent materials and the one or more iteratively labeled ambiguous constituent materials. The method also includes iteratively generating a simulated B0 field map based on the assigned susceptibility values corresponding to each of the one or more distinctive constituent materials and the one or more iteratively labeled ambiguous constituent materials. Further, the method includes determining a similarity metric between the measured B0 field map and the simulated B0 field map during each iteration. Additionally, the method includes identifying the one or more ambiguous constituent materials in each of the one or more dark regions based on the determined similarity metric to ascertain corresponding susceptibility values. Moreover, the method includes correcting the MRI data based on assigned susceptibility values corresponding to the one or more distinctive constituent materials and the ascertained susceptibility values corresponding to the one or more ambiguous constituent materials identified in the MR image. Furthermore, the method includes determining a diagnostic assessment of the target volume based on the corrected MRI data.

In accordance with certain further aspects of the present specification, imaging system configured to image a subject is disclosed. The system includes a scanner configured to scan a target volume of the subject to acquire corresponding MRI data. Further, the system includes a processing subsystem operationally coupled to the scanner, where the processing subsystem is configured to reconstruct a MR image and a measured B0 field map corresponding to the target volume using the MRI data, wherein the MR image includes one or more bright regions and/or one or more dark regions. Moreover, the processing subsystem is configured to identify one or more distinctive constituent materials corresponding to each of the one or more bright regions in the MR image. Additionally, the processing subsystem is configured to iteratively label each of the one or more dark regions in the MR image as one or more ambiguous constituent materials. Furthermore, the processing subsystem is configured to assign susceptibility values corresponding to each of the one or more distinctive constituent materials and the one or more iteratively labeled ambiguous constituent materials. The processing subsystem is also configured to iteratively generate a simulated B0 field map based on the assigned susceptibility values corresponding to each of the one or more distinctive constituent materials and the one or more iteratively labeled ambiguous constituent materials. Further, the processing subsystem is configured to determine a similarity metric between the measured B0 field map and the simulated B0 field map during each iteration. Moreover, the processing subsystem is configured to identify one or more constituent materials in each of the one or more dark regions based on the determined similarity metric to ascertain corresponding susceptibility values. Additionally, the processing subsystem is configured to correct the MRI data based on assigned susceptibility values corresponding to the one or more distinctive constituent materials and the ascertained susceptibility values corresponding to the one or more ambiguous constituent materials identified in the MR image. Further, the processing subsystem is configured to determine a diagnostic assessment of the target volume based on the corrected magnetic resonance imaging data

DRAWINGS

These and other features and aspects of embodiments of the present specification will become better understood when the following detailed description is read with reference to the accompanying drawings in which like characters represent like parts throughout the drawings, wherein.

DETAILED DESCRIPTION

The following description presents a system and method for accurately classifying constituent materials in a target volume of a subject. Specifically, embodiments described herein allow for accurate identification of constituent materials that are traditionally indistinguishable using conventional magnetic resonance imaging (MRI). In particular, embodiments of the present system and method provide an improved MRI workflow to differentiate a metal-induced signal loss from a signal loss caused by air and/or bone, thereby localizing and/or identifying metal objects located in the target volume with greater accuracy.

According to certain aspects of the present specification, regions including metal objects may be differentiated from air and/or bone using a combination of magnitude and phase images obtained from acquired MRI data and/or B0 field maps. It may be noted that a B0 field map corresponds to a map of off-resonance frequencies that are generated due to inhomogeneity in a polarizing magnetic field B0 (hereinafter referred to as B0 field). Typically, the inhomogeneity in the B0 field is caused due to presence of materials with different magnetic susceptibilities proximate to the B0 field. Such inhomogeneity may cause significant susceptibility artifacts in resulting MR images. Therefore, it is desirable to determine an accurate B0 field map that is representative of an actual distribution of constituent materials in an imaged region to compensate for the susceptibility artifacts.

Embodiments of the present system and method aid in determining the actual distribution of constituent materials through a comparison of measured and simulated B0 field maps corresponding to the imaged region. As used herein, the term "measured B0 field" may be used to refer to a graphical representation of off-resonance frequencies that are generated by an actual distribution of constituent materials in an MR image corresponding to a target volume and is determined from acquired MRI data. Further, the term "simulated B0 field" may be used to refer to a graphical representation of off-resonance frequencies that are generated by an assumed distribution of constituent materials, specifically in dark or uncertain regions in the MR image corresponding to the target volume.

Thus, in certain embodiments, the measured B0 field map may be generated from the acquired MRI data. Further, the simulated B0 field map may be generated by iteratively labeling the uncertain regions in the MR image as air, bone, different types of metals, and/or any other constituent materials. The B0 field map may be iteratively simulated until the simulated B0 field map substantially matches the measured B0 field map, thereby providing the actual distribution of constituent materials in the uncertain regions in the MR image. The actual distribution of the constituent materials allows for accurate localization and identification of constituent materials such as air, bone, different types of metals, and/or other implants in the target volume.

Particularly, accurate identification of the constituent materials may aid in determining corresponding susceptibility values to allow for accurate compensation of susceptibility-related artifacts in a final MR image. Furthermore, accurate identification and localization of metal types may aid in automatic selection of specialized MRI pulse sequences that are optimized for high-fidelity imaging of tissues proximal to metal objects. Automatic selection of the specialized MRI pulse sequences allows for better delineation of tissues around the metal objects in a subsequent imaging step irrespective of a skill and/or experience of an operator of an imaging system. Moreover, accurate identification of metal types may aid in enhanced estimation of PET-attenuation values for use in efficient clinical evaluation of a patient.

Although the following description presents embodiments relating to classification of constituent materials for more accurate estimation of PET attenuation values, use of embodiments of the present systems and methods in various other imaging applications is also contemplated. For example, the present systems and methods may be used to supplement diagnostic information acquired by other imaging modalities such as a single photon emission computed tomography (SPECT) system, an ultrasound imaging system, a hybrid MR-PET system, and/or a hybrid MR-SPECT system. An exemplary environment that is suitable for practising various implementations of the present system is described in the following sections with reference to FIG. 1.

Figure 1:
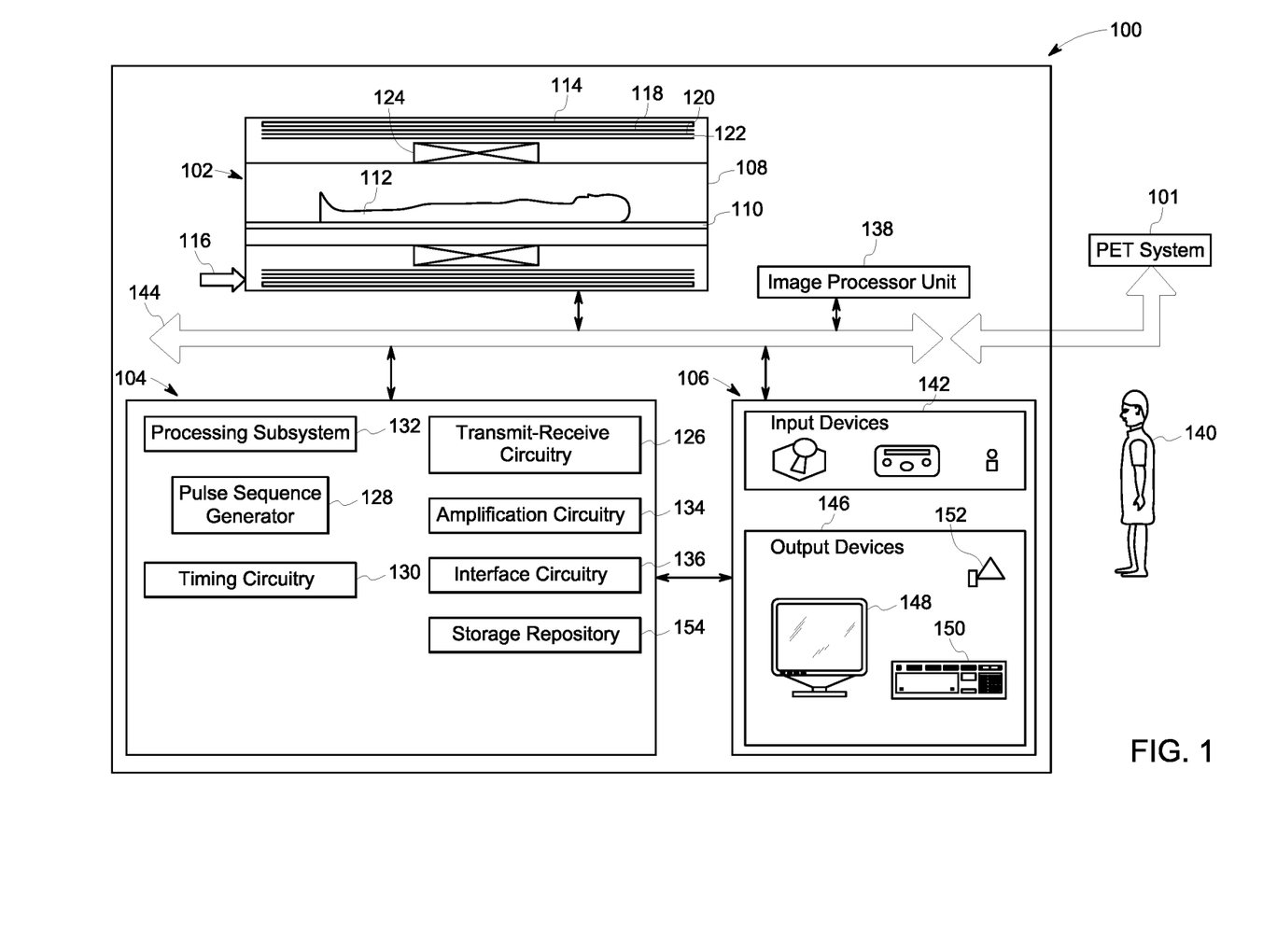
FIG. 1 is a schematic representation of an exemplary imaging system, in accordance with aspects of the present specification.

FIG. 1 illustrates an exemplary MRI system 100 for enhanced imaging of a subject. Particularly, the system 100 may be configured to accurately identify constituent materials in a target volume of the subject for reducing susceptibility-related imaging artifacts, thereby aiding in generation of high quality diagnostic images and clinical information.

In certain embodiments, the high quality diagnostic images and clinical information may be used to complement diagnostic information received from one or more other imaging modalities such as a PET system 101 for use in a more efficient clinical evaluation of the target volume. Accordingly, in one embodiment, the system 100 may be communicatively coupled to the PET system 101. Although FIG. 1 only depicts the PET system 101, in certain embodiments, the system 100 may be communicatively coupled to other imaging modalities such as a SPECT imaging system and/or an ultrasound imaging system. Alternatively, the system 100 may be implemented as a hybrid imaging system such as an MR-PET system, MR-SPECT system, and/or MR-ultrasound system configured to allow for enhanced imaging of the subject.

Particularly, in one embodiment, the MRI system 100 may include a scanner 102, a system controller 104, and an operator interface 106 for imaging the target volume. The target volume, for example, may include biological tissues of interest and/or a non-biological object under evaluation. When used for medical diagnostic imaging, the scanner 102 may further include a patient bore 108 into which a table 110 may be positioned. In one embodiment, the table 110 may be positioned in the patient bore 108 such that the target volume of a patient 112 is positioned at an isocentre of a magnet (not shown) corresponding to the scanner 102.

Further, in certain embodiments, the scanner 102 may also include a series of associated coils for imaging the patient 112. In one embodiment, for example, the scanner 102 may include a primary magnet coil 114 energized via a power supply 116 for generating a primary magnetic field generally aligned with the patient bore 108. The scanner 102 may further include a series of gradient coils 118, 120 and 122 grouped in a coil assembly for generating accurately controlled magnetic fields, the strength of which may vary over a designated field of view of the scanner 102.

Additionally, in one embodiment, the scanner 102 may also include a radiofrequency (RF) coil 124 configured to generate RF pulses for exciting a gyromagnetic material that is typically bound in tissues of the patient 112. In certain embodiments, the RF coil 124 may also serve as a receiving coil. Accordingly, the RF coil 124 may be operationally coupled to transmit-receive circuitry 126 in passive and/or active modes for receiving emissions from the gyromagnetic material and for applying RF excitation pulses, respectively.

In certain embodiments, the system controller 104 may be configured to control operation of the MR coils 118, 120, 122, and 124 for generating the desired magnetic fields and/or for applying the RF excitation pulses. Accordingly, in one embodiment, the system controller 104 may include a pulse sequence generator 128, timing circuitry 130, and a processing subsystem 132. The processing subsystem 132 may be configured to generate and/or control imaging gradient waveforms and RF pulse sequences for use during an MR imaging sequence. In one embodiment, the pulse sequence generator 128 may be configured to generate a T1-weighted, T2-weighted, T2*-weighted, susceptibility-weighted, proton density-weighted, fat selective, water selective, and/or Dixon pulse sequences for acquiring desired MRI data. Particularly, the pulse sequence generator 128 may be configured to generate suitable pulse sequences for acquiring structural MRI information and/or for allowing generation of a B0 field map based on MRI signals received in response to the generated pulse sequences.

Further, in certain embodiments, the system controller 104 may include amplification circuitry 134 and interface circuitry 136 configured to control and/or interface between the pulse sequence generator 128 and the coils of the scanner 102. For example, the amplification circuitry 134 and/or the interface circuitry 136 may be configured to drive the RF coil 124 and amplify corresponding MRI response signals for further processing. The amplified response signals, in turn, may be transmitted to the processing subsystem 132 for determining information for use in image reconstruction. To that end, the processing subsystem 132, for example, may include one or more application-specific processors, graphical processing units (GPUs), digital signal processors (DSPs), microcomputers, microcontrollers, Application Specific Integrated Circuits (ASICs) and/or Field Programmable Gate Arrays (FPGAs).

In certain embodiments, the processing subsystem 132 may be configured to process the response signals generated by excited patient nuclei in response to the MRI pulse sequences. Specifically, the processing subsystem 132 may be configured to demodulate, filter, and/or digitize the response signals for determining information for use in the image reconstruction. Additionally, the processing subsystem 132 may be configured to transmit the digitized information to an image processing unit 138 to allow for reconstruction of desired images of the target volume in the patient 112.

However, as previously noted, when imaging regions include regions such as air-bone interfaces, metal, ceramic, and/or silicone implants, the MRI response signals may not provide distinctive signal intensities for accurate identification of these constituent materials in resulting MR images. For example, MRI of regions proximal to metal implants such as pacemakers or dental fillings may cause excessive heating and/or image artifacts. Specifically, the metal implants may cause significant resonant frequency changes during MRI due to large susceptibility variations between the metal and surrounding tissue. Imaging in and around regions including the metal implants, thus, may result in susceptibility-related imaging artifacts such as substantial signal loss, failure of fat suppression, geometric distortion, and bright pile-up artifacts. MR images of target regions including metal implants, therefore, may not provide accurate diagnostic information, for example, for use in attenuation correction of PET data acquired by the PET system 101 and/or for certain other clinical evaluations.

Accordingly, in certain embodiments, the image processing unit 138 may be configured to process the digitized information corresponding to the acquired MRI response signals to reduce susceptibility-related imaging artifacts in a resulting MR image. To that end, the image processing unit 138, for example, may include one or more application-specific processors, GPUs, DSPs, microcomputers, microcontrollers, ASICs and/or FPGAs. Although FIG. 1 depicts the image processing unit 138 as an independent component, in certain embodiments, the image processing unit 138 may be integrated into the processing subsystem 132 as a software module and/or a hardware module for use in enhanced reconstruction of clinically useful MR images.

Particularly, in one embodiment, the image processing unit 138 may be configured to differentiate regions that include metal objects from air and/or bone regions using a combination of magnitude and phase images obtained from acquired MRI data and B0 field maps. To that end, in certain embodiments, the image processing unit 138 may be configured to classify bright and dark regions in an MR image reconstructed using phase MRI data. Specifically, the image processing unit 138 may be configured to classify the bright regions in the MR image as corresponding to soft tissues and dark regions in the MR image as corresponding to air, bone, and/or metal.

By way of example, the image processing unit 138 may be configured to classify the bright and dark regions using image segmentation techniques such as phase fields, active contours, level-sets, and/or thresholding-based classification. In another example, the image processing unit 138 may be configured to use organ stratification and/or organ context identification to classify regions in the MR image that include air, bone and/or metal. Further, the image processing unit 138 may be configured to filter the phase data corresponding to a particular region in the MR image to more accurately identify if the region belongs to a diamagnetic material or a paramagnetic material.

Additionally, in certain embodiments, the image processing unit 138 may be configured to generate a measured B0 field map based on MRI data acquired using a multi-echo pulse sequence. Specifically, the measured B0 field map may be generated based on the structural MRI information and/or MRI signals received in response to a field-mapping pulse sequence such as the Dixon pulse sequence. As previously noted, a B0 field map corresponds to a map of off-resonance frequencies that are generated due to inhomogeneity in a B0 field. Typically, the inhomogeneity in the B0 field is caused due to presence of materials with different magnetic susceptibilities in proximity of the B0 field. Accordingly, the measured B0 field map may be indicative of a distribution of magnetic susceptibilities in the target volume in accordance with a corresponding distribution of the constituent materials in the target volume.

Although the constituent materials in bright regions of an MR image corresponding to the target volume may be distinctively identified based on the MR signals, the distribution of the constituent materials in one or more dark regions of the MR image may remain uncertain. Thus, in one embodiment, the image processing unit 138 may be configured to accurately identify and/or localize each of the constituent materials in both the bright and dark regions of the MR image. The information related to the identified constituent materials corresponding to each of the bright and dark regions may then be used for compensating for corresponding susceptibility artifacts that are represented by the measured B0 field map.

Particularly, in one embodiment, the image processing unit 138 may be configured to identify distinctive constituent materials corresponding to the bright regions in the MR image. As used herein, the term "distinctive constituent materials" may be used to refer to the constituent materials in the target volume that provide MR response signals, which may be distinctly identified in the MR image based on distinctive intensities and/or other known MRI processing methods. Additionally, the image processing unit 138 may be configured to assign corresponding susceptibility values to the distinctive constituent materials corresponding to the bright regions of the MR image. In one embodiment, for example, the image processing unit 138 may be configured to use one or more lookup tables for determining and assigning the susceptibility values corresponding to each of the distinctive constituent materials. To that end, the lookup tables may include correlations between different types of constituent materials and known susceptibility values to identify and label the distinctive constituent materials corresponding to the bright regions of the MR image.

However, as previously noted, the ambiguous constituent materials in the target volume may fail to provide distinctive MRI response signals, and are thus visualized as dark regions in the MR image. As used herein, the term "ambiguous constituent materials" may be used to refer to the constituent materials in the target volume that are devoid of water molecules, thus providing indistinctive MR response signals, which may not be readily identified in the MR image. Accordingly, in certain embodiments, these ambiguous constituent materials may be identified by analyzing the dark regions in the MR image using an iterative identification technique.

Particularly, in certain embodiments, the image processing unit 138 may be configured to iteratively label each of the dark and/or unknown regions in the MR image as air, bone, different types of metals, and/or any other ambiguous constituent materials in successive iterations of the iterative identification technique. Specifically, in one embodiment, the image processing unit 138 may be configured to iteratively select labels for the one or more dark regions randomly from a stored list of ambiguous constituent materials. The stored list of ambiguous constituent materials, for example, may include air, bone, and/or other materials suitable for use within a patient's body. In an alternative embodiment, however, the labels may be selected during each of the successive iterations based on a priori information such as patient history and/or operator input.

In certain embodiments, the image processing unit 138 may be configured to make an initial assumption when iteratively labeling the dark regions. Particularly, in one embodiment, the image processing unit 138 may be configured to make the initial assumption based on the a priori information, pre-programmed system settings, imaging requirements, and/or user input. For example, when imaging the target volume, presence of even small metal objects may result in significant blooming in a resulting MR image, a subsequent scan using a specialized pulse sequences may be performed to optimally image the dark regions. Accordingly, in one embodiment, the image processing unit 138 may be configured to perform an initial assessment of the dark regions to identify if any of the dark regions include a metal object. Particularly, the image processing unit 138 may be configured to identify a type and/or size of the metal object.

To that end, the image processing unit 138 may be configured to employ one or more reference templates such as a dipole pattern characteristic of a particular type and/or size of a metal. In one embodiment, the dipole patterns characteristic of different types and/or sizes of metals may be stored as a list. The image processing unit 138 may be configured to compare the one or more dark regions in the MR image with the stored dipole patterns and/or fit a dipole pattern observed in a dark region to one of the reference templates using rigid, affine or non-rigid transformations. In certain embodiments, the comparison, for example, may be performed on the entire 3D volume and/or on a slice-by-slice basis. Subsequently, the image processing unit 138 may be configured to identify the type and/or size of metal present in one or more of the dark regions based on the comparison.

Typically, metal objects such as dental implants appear as dark regions that are indistinguishable from bone and air in an MR image. Accordingly, in one embodiment, the image processing unit 138 may be configured to employ MR phase images determined from the acquired MRI data for differentiating between bone, air, and the metal object. Particularly, the image processing unit 138 may be configured to pre-process the MR phase images, for example via low-pass filtering, to remove any contribution of global phase while retaining local susceptibility phase changes. Retention of only local susceptibility values enhances a distinction between bone, air, and the metal object in the MR phase images.

Particularly, owing to a difference in material properties of air and the metal object in the presence of a B0 magnetic field, each of the air and the metal object produces a different change in the B0 magnetic field. Accordingly, in one embodiment, the image processing unit 138 may be configured to determine the change in the B0 magnetic field at different spatial locations corresponding to different regions of the pre-processed phase MR image. Particularly, the image processing unit 138 may be configured to determine the change in the B0 magnetic field to distinguish between air and the metal object in the pre-processed phase MR image and determine corresponding susceptibility values.

In one embodiment, the image processing unit 138 may be configured to model the iterative identification and corresponding determination of susceptibility values for the one or more dark regions as an inverse problem. By way of example, where a selected dark region includes the metal object, the change in the B0 magnetic field may correspond to magnetization induced due to the metal object in presence of an external magnetic field. The induced magnetization, for example, may be represented as an inverse problem using equation (1):

$$\vec{M} = \chi \vec{H} \quad (1)$$

where $\vec{M}$ corresponds to the induced magnetization determined from the pre-processed MR phase image, $\vec{H}$ corresponds to magnetization due to the applied B0 magnetic field, and $\chi$ corresponds to a susceptibility matrix, where each element of the susceptibility matrix $\chi$ refers to a determined susceptibility in the direction of change in a local magnetic field with respect to an applied B0 magnetic field.

Given the values of the induced magnetization M □ and magnetization due to the applied B0 magnetic field H □, in one embodiment, the image processing unit 138 may be configured to model the computation of the matrix $\chi$ as an inverse problem. Particularly, the image processing unit 138 may be configured to determine a signature of the magnetic susceptibility in a selected dark region based on a determined solution of the inverse problem defined in equation (1). In certain embodiments, the determined signature of the magnetic susceptibility may be used to distinguish between air and the metal object in the target volume. Specifically, the signature of the magnetic susceptibility may be used to identify a specific metal object present in the selected dark region.

Subsequently, the image processing unit 138 may be configured to assign a susceptibility value corresponding to the identified metal to the selected dark region. Similarly, in further iterations, one or more other labels and corresponding susceptibility values may also be assigned to one or more of the other dark regions.

In one embodiment, the susceptibility values assigned to the bright and dark regions in the MR image provide an assumed susceptibility distribution corresponding to the target volume for a particular iteration of the iterative identification technique. According to certain aspects of the present specification, the image processing unit 138 may be configured to iteratively generate a simulated B0 field map based on the assumed susceptibility distribution. For example, the image processing unit 138 may be configured to convert the assumed susceptibility distribution to the simulated B0 field map using a slice-by-slice Fourier domain transformation. Alternatively, the image processing unit 138 may be configured to convert the assumed susceptibility distribution to the simulated B0 field map using an iterative finite element method, a finite difference method, a perturbative approximations method, and/or any other suitable method.

Particularly, the image processing unit 138 may be configured to iteratively simulate the B0 field map based on the assumed susceptibility distribution until the simulated B0 field map corresponding to a particular iteration substantially matches the measured B0 field map. In one embodiment, for example, a similarity metric such as a normalized correlation or a semantic similarity ensemble may be used to correlate the measured B0 field map to the simulated B0 field map. Specifically, the image processing unit 138 may be configured to identify the simulated B0 field map that has the best or the closest match to the measured B0 field map based on the similarity metric. The simulated B0 field map may then be used to localize and identify the actual distribution of the constituent materials in the dark regions of the MR image. Particularly, in certain embodiments, information corresponding to the one or more ambiguous constituent materials identified in a dark region may be used to interpolate labels for other dark regions in the vicinity, for example, using a registered anatomical atlas.

As previously noted, accurate identification of the constituent materials may aid in determining corresponding susceptibility values to allow for accurate compensation of susceptibility-related artifacts in a final MR image. Furthermore, accurate identification and localization of metal types may aid in automatic selection of specialized MRI pulse sequences that are optimized for high-fidelity imaging of tissues proximal to metal objects. By way of example, such specialized sequences may include a multi-acquisition with variable resonance image combination (MAVRIC) pulse sequence and/or a slice-encoding metal artifact correction (SEMAC) pulse sequence.

In one embodiment, the specialized MRI pulse sequences may allow for better delineation of tissues around metal objects in a subsequent imaging step irrespective of a skill and/or experience of the operator. For example, use of the MAVRIC pulse sequence may allow for more accurate localization of metal related artifacts in an MR image. In certain embodiments, the image processing unit 138 may be configured to apply a segmentation method to the localized metal related artifacts in the MR image to accurately identify metal regions and estimate corresponding sizes. Furthermore, use of the MAVRIC pulse sequence may aid in measurement of a more accurate B0 field map, which in turn, may allow classification of specific types of metals through a comparison of the measured B0 field map and a simulated B0 field map as described herein. Such a comparison may quickly allow for accurate identification of specific metal types since metals that may be suitable for introduction into a patient's body are limited in number. Accurate identification of metal types and sizes, in turn, may allow for accurate MR image reconstruction and/or accurate PET attenuation correction.

Although, certain embodiments of the system 100 may allow for automatic selection of pulse sequences, in certain other embodiments, the system 100 may be configured to allow a medical practitioner 140 to select a suitable pulse sequence for imaging regions close to a metal implant. To that end, the operator interface 106 may further include one or more input devices 142 that are operatively coupled to the MRI system 100 and/or the PET system 101 via a communications link 144, such as a backplane or Internet. The input devices 142, for example, may include a keyboard, a mouse, a trackball, a joystick, a touch-activated screen, a light wand, a control panel, and an audio input device such as a microphone associated with corresponding speech recognition circuitry. In one embodiment, the input devices 142 may further include an interactive graphical user interface (GUI) that may allow the medical practitioner 140 to select a desired view of the metal implant and/or the target volume in the same or a subsequent scan. The input devices 142 may also allow the medical practitioner 140 to request for image-derived clinical information such as tissue characteristics for assessing and/or continual monitoring of a pathological condition of the patient 112.

In certain embodiments, the image processing unit 138 may be configured to determine the requested information from the accurately reconstructed MR images and/or PET images. Further, the image processing unit 138 may be configured to provide the medical practitioner 140 with the requested information in real-time through one or more output devices 146. In certain embodiments, the output devices 146, for example, may include a display 148, a printer 150, and/or an audio output device 152.

In one embodiment, the display 148 may be integrated into wearable eyeglasses, or may be ceiling or cart mounted to allow the medical practitioner 140 to observe the reconstructed MR and/or PET images and other medically relevant information during imaging. Accordingly, in certain embodiments, the image processing unit 138 may be configured to transmit the requested information to the medical practitioner 140 as a visual report on the display 148 and/or the printer 150. Alternatively, the image processing unit 138 may be configured to convey the requested information to the medical practitioner 140 audibly through the audio output device 152.

Additionally, in certain embodiments, the image processing unit 138 may be configured to store the requested information in a storage repository 154. The storage repository 154 may be configured to store specialized MRI pulse sequences, determined similarity metrics, lookup tables that include stored correlations between types of constituent materials and known susceptibility values, acquired MRI and PET data, and/or reconstructed MR and PET images. Accordingly, in certain embodiments, the storage repository 154 may include devices such as a hard disk drive, a floppy disk drive, a compact disk-read/write (CD-R/W) drive, a Digital Versatile Disc (DVD) drive, a flash drive, and/or a solid-state storage device.

It may be noted that in the embodiment depicted in FIG. 1, the input devices 142, the output devices 146, and the storage repository 154 are shown as being part of the MRI system 100. However, in an alternative embodiment, the input devices 142, the output devices 146, and/or the storage repository 154 may be communicatively coupled to both the MRI system 100 and the PET system 101. In such an embodiment, shared use of the input devices 142, the output devices 146, and/or the storage repository 154 may aid in conserving floor space and/or simplifying an imaging workflow for generating accurate diagnostic information.

Embodiments of the present system 100, thus, allow for robust and reproducible classification of constituent materials such as air, bone and/or metal that are conventionally indistinguishable in an MR image. Particularly, accurate identification of the constituent materials may aid in determining corresponding susceptibility values to allow for accurate compensation of susceptibility-related artifacts in a final MR image. Furthermore, accurate identification and localization of metal types may aid in automatic selection of specialized MRI pulse sequences that are optimized for high-fidelity imaging of tissues proximal to metal objects. Particularly, automatic selection of the specialized MRI pulse sequences allows for better delineation of tissues around metal objects in a subsequent imaging step irrespective of a skill and/or experience of an operator.

Moreover, accurate information corresponding to locations and types of metal objects in the target volume may be used to supplement patient information derived from other imaging systems and/or information storage systems for a detailed evaluation of the target volume. For example, accurate information corresponding to locations and types of the metal objects may aid in more accurate estimation of PET-attenuation values even in regions close to the metal objects, thereby allowing for more efficient bio-molecular evaluation of a patient. An exemplary embodiment of a method for MR imaging for use in accurately classifying different constituent materials, in accordance with certain aspects of the present specification, will be described in greater detail with reference to FIG. 2.

Figure 2:
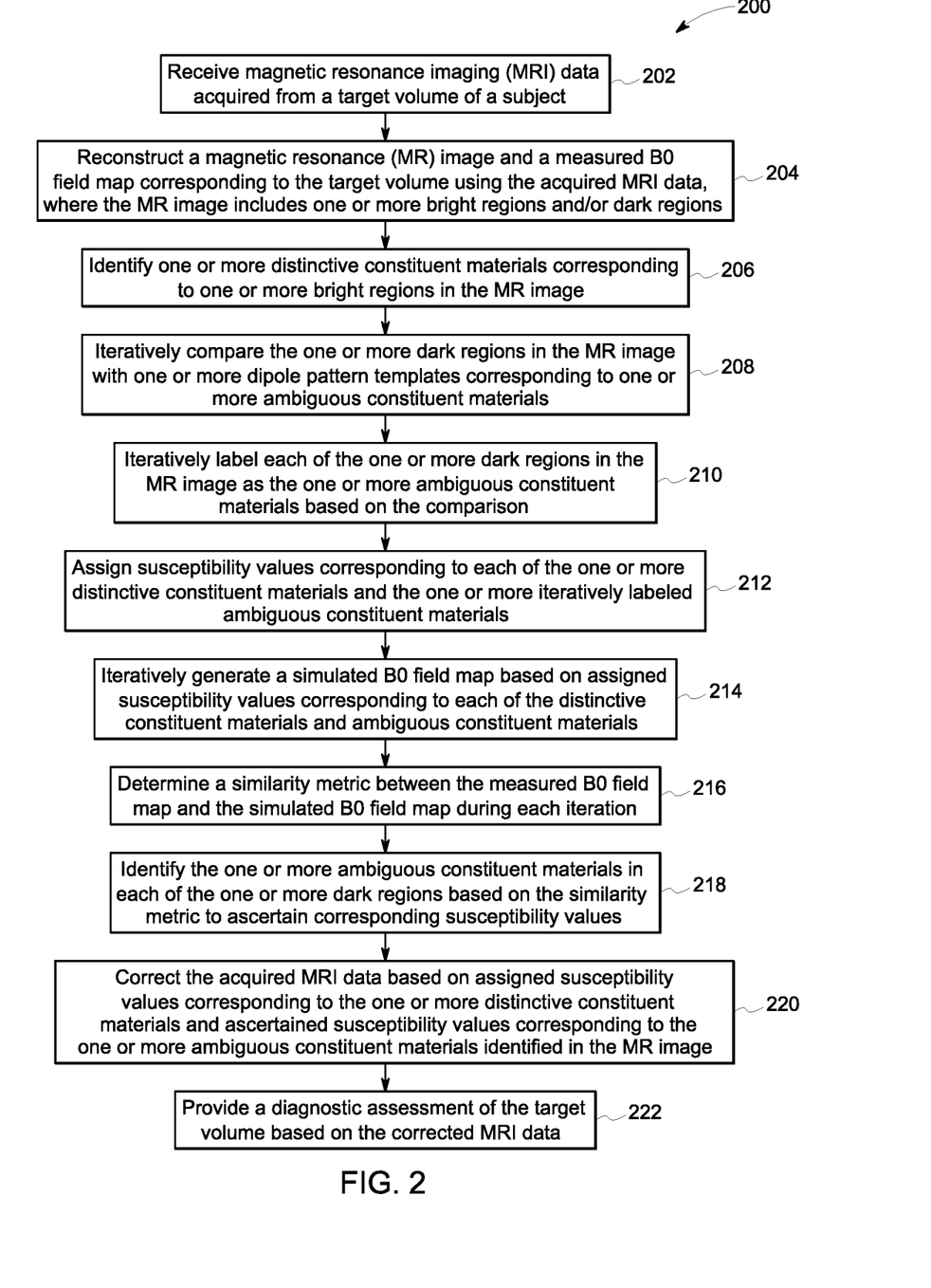
FIG. 2 is a flow chart illustrating an exemplary method for MR imaging, in accordance with aspects of the present specification.

FIG. 2 illustrates a flow chart 200 depicting an exemplary method for MR imaging. In the present specification, embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract data types.

Additionally, embodiments of the exemplary method may also be practised in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 2, the exemplary method is illustrated as a collection of blocks in a logical flow chart, which represents operations that may be implemented in hardware, software, or combinations thereof. The various operations are depicted in the blocks to illustrate the functions that are performed, for example, during steps of reconstructing a magnetic resonance image and a measured B0 field map, accurately identifying one or more ambiguous constituent materials, and/or determining a diagnostic assessment of the target volume in the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIG. 1.

Embodiments of the present method may allow for accurate identification of constituent materials that are traditionally indistinguishable using conventional MR imaging. The method begins at step 202, where MRI data acquired from a target volume of a subject using one or more MRI pulse sequences is received. The MRI pulse sequences used for acquiring the MRI data, for example, may include a spin echo MRI sequence, a multi-echo MR acquisition sequence, and/or a gradient echo MRI sequence. Moreover, the target volume, for example, may include biological tissues such as cardiac tissues or liver tissues of a patient. Alternatively, the target volume may correspond to a portion of a non-biological object such as pipes made of synthetic polymers. For clarity, the present method is described herein with reference to a medical diagnostic imaging application for imaging the target volume of the subject.

Subsequently, at step 204, an MR image and a measured B0 field map corresponding to the target volume may be reconstructed using the acquired MRI data. The MR image, for example, may include one or more bright regions that correspond to one or more distinctive constituent materials and/or one or more dark regions that correspond to one or more ambiguous constituent materials in the target volume.

In one embodiment, the desired MR image of the target volume may be reconstructed using MRI data acquired using a spin echo pulse sequence, ultra short echo (UTE) pulse sequence, and/or a gradient echo pulse sequence. Additionally, in certain embodiments, a B0 field map corresponding to the target volume may be reconstructed using one or more MRI pulse sequences that may be specifically selected by a medical practitioner. For example, in one embodiment, the measured B0 field map may be reconstructed using MRI data acquired using a multi-echo acquisition sequence. In an alternative embodiment, however, both the MR image and the measured B0 field map may be generated using the MRI data acquired using the same MRI pulse sequence, for example, the spin echo pulse sequence. It may be noted that the MR image and the measured B0 field map may be representative of one or more distinctive and/or ambiguous constituent materials present in the target volume.

Accordingly, at step 206, one or more distinctive constituent materials corresponding to each of the one or more bright regions in the MR image may be identified. As previously noted, the bright regions in the MR image may include certain distinctive constituent materials such as soft tissues, water, and/or fat that include water molecules. Imaging the target volume that includes such distinctive constituent materials generates MRI response signals having different signals intensities and/or brightness, and therefore, may be readily visualized in the MR image.

For example, response signals received from cardiac tissues may have a particular signal intensity that is different from a signal intensity of response signals received from lung tissues. The different signal intensities may be used to distinctly classify constituent materials in the imaged region. Particularly, in one embodiment, the distinctive constituent materials in the MR image may be identified using image segmentation techniques such as phase-fields, active contours, level-sets, and/or thresholding-based classification. In certain other embodiments, the distinctive constituent materials in the MR image may be identified using clustering, atlas matching, and/or other suitable machine learning-based methods.

As previously noted, the dark regions in the MR image may correspond to certain ambiguous constituent materials that fail to provide MR response signals in response to the MRI pulse sequence. Since many of the ambiguous constituent materials may provide similarly indistinctive and/or dark MRI response signals, these ambiguous constituent materials in the target volume may not be identified using conventional MRI processing. Accordingly, in one embodiment, the dark regions may be initially classified based on corresponding shapes to determine if they fit a distinctive pattern. Alternatively, classification of the dark regions may be modeled and solved as an inverse problem.

Further, at step 208, the one or more dark regions in the MR image may be iteratively compared with one or more dipole pattern templates corresponding to one or more ambiguous constituent materials. In one embodiment, the dipole pattern templates correspond to magnetic susceptibility patterns characteristic of different types and/or sizes of metal objects. Accordingly, the dipole patterns corresponding to different types and sizes of metal objects are distinctive and effectively visualized during MRI. By way of example, FIGS. 3A, 3B, and 3C depict exemplary MR images that visualize a dipole pattern exhibited by a metal object.

Figure 3A:
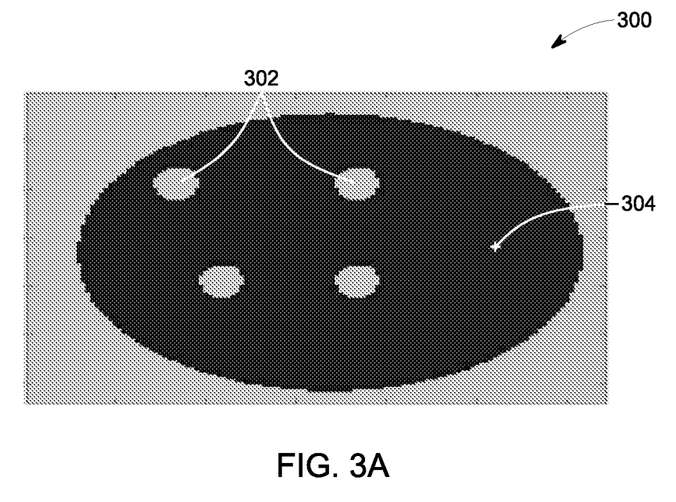
FIG. 3A is a water-filled phantom that includes a plurality of air-filled vials and a metal object.
Figure 3B:
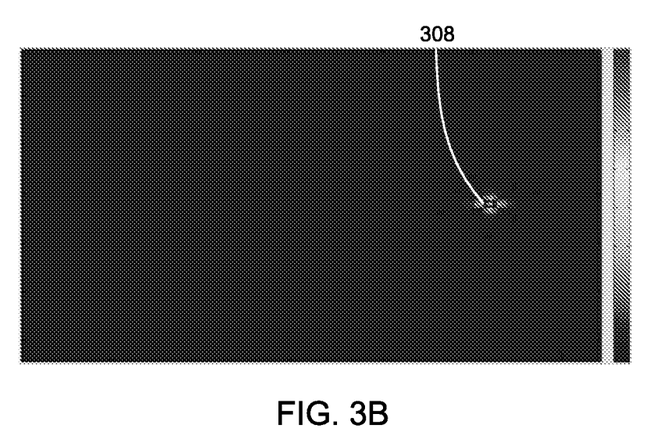
FIGS. 3B and 3C illustrate exemplary MR images corresponding to the water-filled phantom of FIG. 3A.
Figure 3C:
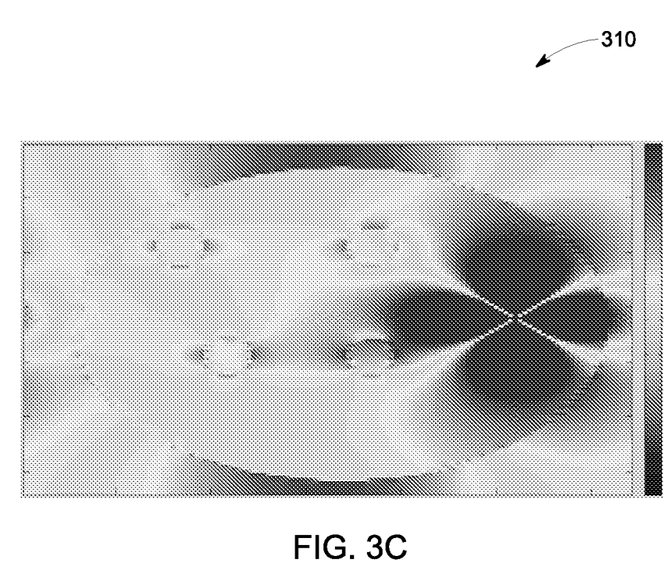

Particularly, FIG. 3A corresponds to a water-filled phantom 300 that includes four air-filled vials 302 and a small iron oxide particle 304. Further, FIG. 3B illustrates an MR image 306 corresponding to the water-filled phantom 300 of FIG. 3A. As depicted in FIG. 3B, a dipole pattern 308 exhibited by the iron oxide particle 304 may be distinctively visualized along a B0 direction that corresponds to a coronal slice for a supine patient. Additionally, FIG. 3C illustrates a magnified view 310 of the water phantom 306 depicted in FIG. 3B for enhanced visualization of the dipole pattern 308 of FIG. 3B. As depicted in FIG. 3C, even the small iron oxide particle 304 of FIG. 3A causes a significant and distinctive dipole pattern 308 in a resulting MR image.

Accordingly, with returning reference to FIG. 2, the comparison of the dark regions to known dipole patterns may provide an indication of whether a metal object is present in one or more of the dark regions. Additionally, the comparison may also allow for identification of a probable location, type and/or size of a metal object in the dark regions.

In one embodiment, the comparison may entail locating the dipole patterns in the dark regions using a scale-invariant pattern matching method. In alternative embodiments, other reference templates that may correspond to characteristic patterns corresponding to other ambiguous constituent materials may be used. The characteristic patterns may be identified in the dark regions using the scale-invariant pattern matching method.

Subsequently, at step 210, each of the one or more dark regions in the MR image may be labeled as one or more ambiguous constituent materials based on the comparison performed at step 208. In certain embodiments, the dark regions in the MR image may be pre-processed, as described with reference to step 208, to determine a more probable label for each dark region. Additionally, organ stratification and/or organ context-based identification may be used to evaluate the dark regions that may include air, bone and/or metal. The one or more dark regions in the MR image may then be iteratively labeled based on a probability of presence of an ambiguous constituent material determined based on the pre-processing. For example, in an initial iteration when imaging the head region, the iterative labels may include labels corresponding to selected ambiguous constituent materials that may be typically found in dental clips and/or head sutures, and their corresponding sizes. In ensuing iterations, the dark regions may be relabeled with other suitable sizes and/or types of the selected ambiguous constituent materials.

Alternatively, in certain embodiments, the dark regions may be labeled using an iterative identification technique. For example, during successive iterations of the iterative identification technique, one or more of the dark regions may be randomly assigned labels that are selected from a pre-programmed or predetermined list of ambiguous constituent materials. The list, for example, may include ambiguous constituent materials such as air, bone and/or one or more metals including ferromagnetic materials, titanium alloys or dental implants that are suitable for use within a patient's body.

Subsequently at step 212, susceptibility values corresponding to each of the one or more distinctive constituent materials and the each of the one or more iteratively labeled dark regions may be assigned. In one embodiment, for example, the susceptibility values corresponding to the distinctive and ambiguous constituent materials may be determined using lookup tables stored in an associated memory device such as the storage repository 154 of FIG. 1. The lookup tables may store one or more correlations between different constituent materials and their corresponding susceptibility values, and thus, may be used to make appropriate assignments to each of the bright and dark regions in the MR image.

Further, at step 214, a simulated B0 field map may be generated based on the assigned susceptibility values corresponding to each of the one or more distinctive constituent materials and the one or more iteratively labeled ambiguous constituent materials. In one embodiment, the susceptibility values determined for each of the distinctive constituent materials in the bright regions and the ambiguous constituent materials assumed to be present in the dark regions during a particular iteration may be used to generate a susceptibility distribution map corresponding to the MR image. The susceptibility distribution map may then be used to determine a location, size, and/or distribution of different constituent materials in the target volume.

Particularly, in one embodiment, the susceptibility distribution map may be used to generate the simulated B0 field map corresponding to the assumed distribution of different types and/or sizes of the ambiguous constituent materials in the target volume. In one example, the simulated B0 field map may be generated from the susceptibility distribution map using a slice-by-slice Fourier domain transformation, an iterative finite element method, a finite difference method, a perturbative approximations method, and/or any other suitable method.

Additionally, at step 216, a similarity metric between the measured B0 field map and the simulated B0 field map may be determined during each iteration. In one embodiment, the measured B0 field map and the simulated B0 field map generated during each iteration may be correlated using a similarity metric such as a normalized correlation or a semantic similarity ensemble. The similarity metric may be employed to identify the iteratively simulated B0 field map that has the best correlation and/or is the closest match to the measured B0 field map.

Further, at step 218, the one or more ambiguous constituent materials in each of the one or more dark regions may be identified based on the similarity metric determined at step 216 and corresponding susceptibility values may be ascertained. Specifically, the assumed distribution of different types and/or sizes of the ambiguous constituent materials in the simulated B0 field map having the best correlation with the measured B0 field map may be used to identify a type and/or a size of one or more of the ambiguous constituent materials actually present in the dark regions of MR image. Moreover, corresponding susceptibility values may be ascertained using a lookup table that includes stored correlations between different types of constituent materials and known susceptibility values.

In certain embodiments, the one or more constituent materials in a selected dark region and corresponding susceptibility values may be identified based on the one or more ambiguous constituent materials identified in the one or more dark regions adjacent to the selected dark region and/or by using an anatomical atlas. In certain other embodiments, the iterative labeling and corresponding ascertaining of accurate susceptibility values for the one or more bright and/or dark regions may be further refined and modeled as an inverse problem. Solving the inverse problem aids in determining a signature of the magnetic susceptibility corresponding to a selected bright or dark region in the MR image. The determined signature of the magnetic susceptibility, in turn, allows for enhanced differentiation between traditionally indistinguishable regions such as regions including air and metal implants in the MR image.

Particularly, accurate identification of the dark regions allows for reconstruction of enhanced MR images, while also aiding in optimizing imaging parameters for a subsequent scan of the target volume. By way of example, in certain embodiments, where the target volume is determined to include a metal object, the acquired MRI data corresponding to regions that are proximal to the metal object may include substantial distortions. Accordingly, upon detecting presence of a metal implant in one or more of the dark regions, an MRI system may be configured to allow for automatic selection of specialized MRI pulse sequences such as MAVRIC and/or SEMAC for a subsequent scan of the target volume.

Typically, the specialized pulse sequences allow for high-fidelity imaging of tissues proximal to metal objects irrespective of a skill and/or experience of an operator. Accordingly, use of the specialized pulse sequences may allow for enhanced localization of the metal object in the MR image and estimation of a corresponding size. Furthermore, use of the specialized pulse sequence may aid in measurement of a more accurate B0 field map, which in turn, may allow classification of specific types of metals through a comparison of the measured B0 field map and the simulated B0 field map, as described with reference to steps 208-218. Such a comparison may allow for rapid and accurate identification of specific metal types since metals suitable to be introduced into a patient's body are limited in number.

Generally, the metal object may cause field inhomogeneities that produce off-resonance frequencies at each voxel, in turn leading to blurring and/or distortion in the resulting MRI images. Accurate identification of a type and a size of the metal object, thus, may aid in correction of the field inhomogeneities in the MR images. Additionally, accurate identification of a type and a size of the metal object may allow for accurate MR image reconstruction and/or accurate PET attenuation correction.

Accordingly, at step 220, the acquired MRI data may be corrected based on the assigned susceptibility values corresponding to the one or more distinctive constituent materials and the ascertained susceptibility values corresponding to the one or more ambiguous constituent materials identified in the MR image. As previously noted, accurate susceptibility values for each of the identified constituent materials may be determined using lookup tables or other stored correlations. The accurate susceptibility values, thus determined, may then be used to correct for susceptibility-related distortions in the acquired MRI data.

Furthermore, at step 222, a diagnostic assessment of the target volume may be provided based on the corrected MRI data. Specifically, the corrected MRI data may be used for accurate MR image reconstruction of the target volume despite presence of paramagnetic and/or diamagnetic materials such as metals in the target volume. Additionally, in certain embodiments, the corrected MRI data may be used to supplement and/or correct diagnostic information such as PET attenuation values determined using other imaging modalities such as the PET system 101 of FIG. 1. Availability of an accurate MR image and/or PET attenuation values, in turn, may provide accurate clinical information to assess a pathological condition of the patient without need for additional MRI and/or PET acquisitions. Embodiments of the present method, thus, allows for robust and reproducible classification of constituent materials such as air, bone and/or metal that are conventionally indistinguishable in an MR image.

FIGS. 4A, 4B, 4C, and 4D depict examples of conventional MR images corresponding to a target volume. The target volume, for example, corresponds to a sinus region proximal to a petrous part of a temporal bone that is pneumatic, and thus, often generates false positive MR response signals indicative of air. Moreover, the target volume may include a denture 408, which may further distort the MR images corresponding to the target volume.

Figure 4A:
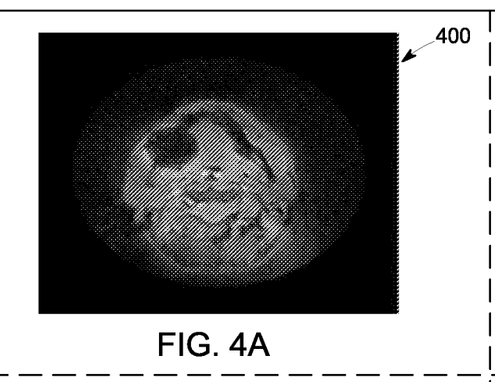
FIGS. 4A, 4B, 4C, and 4D illustrate exemplary images of a target volume generated using a conventional MRI method and an ultra-short echo pulse sequence, in accordance with aspects of the present specification.

Particularly, FIG. 4A may correspond to a magnitude-based MR image 400 corresponding to the target volume that is generated using traditional long echo time pulse sequences (for example, of about 2.3 milliseconds (ms)). Similarly, FIG. 4B may correspond to a magnitude-based MR image 402 corresponding to the target volume that is generated using zero echo time (ZTE) pulse sequences. Further, FIGS. 4C and 4D may correspond to phase MR images 404 and 406, respectively that are generated using a traditional long echo time pulse sequence and a ZTE pulse sequence, respectively.

Figure 4B:
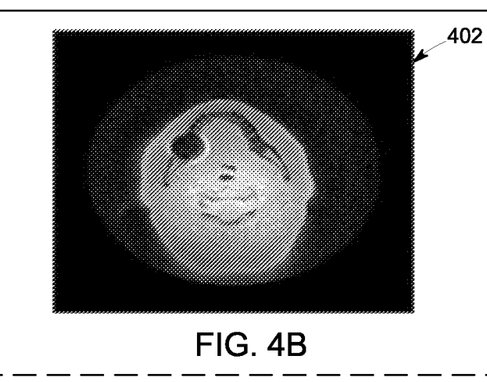
Figure 4C:
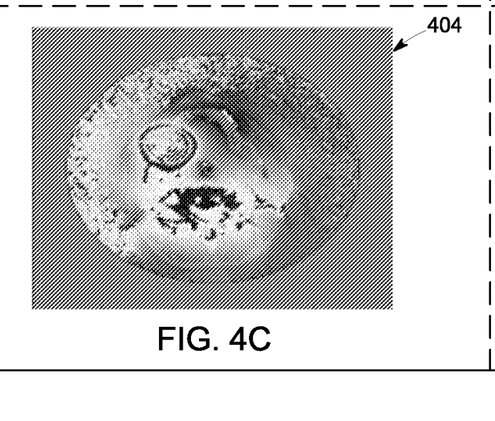

As evident from the depictions of FIGS. 4A and 4C, imaging the target volume using traditional pulse sequences results in signal loss and distortion due to presence of the denture 408 in the target volume. The signal loss and distortion, in turn, cause the resulting MR images 400 and 404 depicted in FIGS. 4A and 4C to include indistinct visualization of the sinus region. Further, imaging the target volume using ZTE pulse sequences may allow for slightly better localization of the denture 408 as compared to traditional long echo pulse sequences, as depicted in FIGS. 4B and 4D.

Figure 4D:
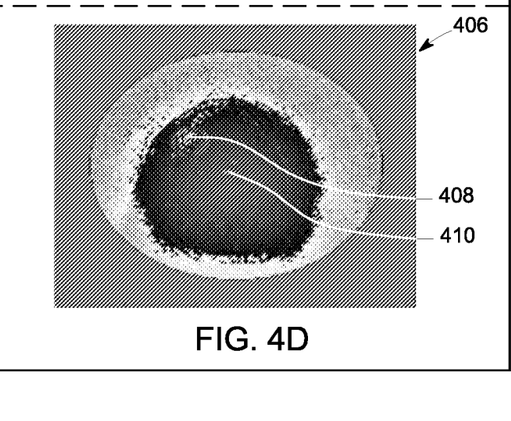

Additionally, use of the ZTE pulse sequences may also provide a smooth background phase to allow for a texture based analysis of the MR images 402 and 406 depicted in FIGS. 4B and 4D. In the embodiment depicted in FIG. 4D, the texture based analysis may aid in differentiating the denture 408 from an air pocket 410 in the target volume. Use of the embodiments of the present method may allow for more efficient visualization of the morphological structures such as the sinus region via accurate identification of a location, type, and/or size of an implant such as the denture 408.

Embodiments of the present system and method, thus, allows for accurate identification of traditionally indistinguishable constituent materials in an MR image. In particular, embodiments described herein provide an improved MRI workflow to differentiate a metal-induced signal loss from a signal loss caused by air and/or bone, thereby localizing and/or identifying metal objects with greater accuracy. The improved MRI workflow allows for automatic selection of specialized MRI sequences for better visualization of conventionally distorted regions. Particularly, use of the specialized pulse sequences may allow for accurate localization and estimation of a size and type of an implant or a distortion-causing object irrespective of a skill or experience of an operator. The accurate localization, size, and type information, in turn, may be used for accurate correction of a resulting susceptibility-related distortion in the acquired MRI data. The corrected values may then be advantageously used to provide a more informed clinical assessment of the patient.

It may be noted that the foregoing examples, demonstrations, and process steps that may be performed by certain components of the present systems, for example by the system controller 104, the processing subsystem 132, and the image processing unit 138 of FIG. 1, may be implemented by suitable code on a processor-based system. To that end, the processor-based system, for example, may include a general-purpose or a special-purpose computer. It may also be noted that different implementations of the present specification may perform some or all of the steps described herein in different orders or substantially concurrently.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of various embodiments of the present disclosure may be shown in and/or described with respect to some drawings and not in others, this is for convenience only. It is to be understood that the described features, structures, and/or characteristics may be combined and/or used interchangeably in any suitable manner in various embodiments, for example, to construct additional assemblies and MRI methods.

While only certain features of the present disclosure have been illustrated and described herein, many modifications and changes will occur to those skilled in the art. It is, therefore, to be understood that the appended claims are intended to cover all such modifications and changes as fall within the true spirit of the invention.

We claim:

1. A method for imaging a subject, comprising:
   reconstructing a magnetic resonance image and a measured B0 field map corresponding to a target volume in the subject using magnetic resonance imaging data acquired from the target volume, wherein the magnetic resonance image comprises one or more bright regions and one or more dark regions;
   identifying one or more distinctive constituent materials corresponding to each of the one or more bright regions in the magnetic resonance image;
   iteratively labeling each of the one or more dark regions in the magnetic resonance image as one or more ambiguous constituent materials;
   assigning susceptibility values corresponding to each of the one or more distinctive constituent materials and the one or more iteratively labeled ambiguous constituent materials;

iteratively generating a simulated B0 field map based on the assigned susceptibility values corresponding to each of the one or more distinctive constituent materials and the one or more iteratively labeled ambiguous constituent materials;

determining a similarity metric between the measured B0 field map and the simulated B0 field map during each iteration; and identifying the one or more ambiguous constituent materials in each of the one or more dark regions based on the determined similarity metric to ascertain corresponding susceptibility values.

2. The method of claim 1, wherein reconstructing the magnetic resonance image and the measured B0 field map comprises:

generating the magnetic resonance image using one or more spin echo imaging pulse sequences, one or more gradient echo sequences, or a combination thereof; and generating the measured B0 field map using one or more multi-echo acquisition pulse sequences.

3. The method of claim 1, wherein identifying the one or more distinctive constituent materials comprises processing the magnetic resonance image via image segmentation, organ stratification, organ context identification, phase-fields based classification, active contours based classification, level-sets based classification, thresholding-based classification, or combinations thereof.

4. The method of claim 1, wherein iteratively labeling each of the one or more dark regions comprises providing an initial assessment of the one or more dark regions based on iteratively comparing corresponding shapes to one or more dipole pattern templates associated with the one or more ambiguous constituent materials.

5. The method of claim 4, wherein iteratively comparing the corresponding shapes to the one or more dipole pattern templates comprises matching the corresponding shapes of the one or more dark regions with the one or more dipole pattern templates using a rigid transformation, an affine transformation, a non-rigid transformation, or combinations thereof.

6. The method of claim 4, further comprising receiving the one or more dipole pattern templates corresponding to one or more metal objects, one or more sizes corresponding to the one or more metal objects, or a combination thereof.

7. The method of claim 1, wherein iteratively labeling each of the one or more dark regions in the magnetic resonance image comprises labeling the one or more dark regions in the magnetic resonance image with one or more types corresponding to the one or more ambiguous constituent materials, one or more sizes corresponding to the one or more ambiguous constituent materials, or a combination thereof.

8. The method of claim 1, wherein iteratively labeling each of the one or more dark regions in the magnetic resonance image comprises iteratively selecting the one or more ambiguous constituent materials from a plurality of ambiguous constituent materials.

9. The method of claim 1, wherein assigning the susceptibility values corresponding to each of the one or more distinctive constituent materials and the one or more ambiguous constituent materials comprises using a lookup table, and wherein the lookup table comprises stored correlations between the one or more distinctive constituent materials, the one or more ambiguous constituent materials, or a combination thereof, and corresponding susceptibility values.

10. The method of claim 1, further comprising modeling the iterative labeling of each of the one or more dark regions and assigning susceptibility values corresponding to each of the one or more distinctive constituent materials and the one or more iteratively labeled ambiguous constituent materials as an inverse problem.

11. The method of claim 10, further comprising:

generating one or more phase magnetic resonance images from the magnetic resonance imaging data, the magnetic resonance image, or a combination thereof;

pre-processing the one or more phase magnetic resonance images to remove a corresponding contribution of global phase information while retaining local susceptibility phase changes; and computing a susceptibility matrix, wherein each element in the susceptibility matrix corresponds to a determined susceptibility in a direction of change in a local magnetic field that induces magnetization in the target volume with respect to an externally applied B0 magnetic field; and determining a solution of the inverse problem based on the induced magnetization determined from the one or more pre-processed phase magnetic resonance images, a magnetization caused by the externally applied B0 magnetic field, and the computed susceptibility matrix.

12. The method of claim 1, wherein iteratively generating the simulated B0 field map based on the assigned susceptibility values comprises:

generating a susceptibility distribution map corresponding to the magnetic resonance image based on the assigned susceptibility values corresponding to each of the one or more distinctive constituent materials and the one or more iteratively labeled ambiguous constituent materials; and generating the simulated B0 field map from the susceptibility distribution map using a slice-by-slice Fourier domain transformation.

13. The method of claim 1, wherein the similarity metric comprises a normalized correlation, a semantic similarity ensemble, or a combination thereof.

14. The method of claim 1, wherein identifying the one or more ambiguous constituent materials in each of the one or more dark regions comprises:

localizing a metal object located in the target volume; and determining one or more of a size and a type of the localized metal object.

15. The method of claim 14, further comprising automatically initiating specialized imaging pulse sequences to image the one or more dark regions in the target volume proximal the metal object.

16. The method of claim 1, further comprising identifying one or more constituent materials in at least one dark region selected from the one or more dark regions based on the one or more ambiguous constituent materials identified in the one or more dark regions adjacent to the at least one selected dark region.

17. The method of claim 1, wherein identifying the one or more ambiguous constituent materials comprises identifying one or more of air, bone, and a metal object in the target volume.

18. An imaging system configured to image a subject, comprising:

a scanner configured to scan a target volume of the subject to acquire corresponding magnetic resonance imaging data;

a processing subsystem operationally coupled to the scanner, wherein the processing subsystem is configured to:

reconstruct a magnetic resonance image and a measured B0 field map corresponding to the target volume using the magnetic resonance imaging data, wherein the magnetic resonance image comprises one or more bright regions and one or more dark regions;

identify one or more distinctive constituent materials corresponding to each of the one or more bright regions in the magnetic resonance image;

iteratively label each of the one or more dark regions in the magnetic resonance image as one or more ambiguous constituent materials;

assign susceptibility values corresponding to each of the one or more distinctive constituent materials and the one or more iteratively labeled ambiguous constituent materials;

iteratively generate a simulated B0 field map based on the assigned susceptibility values corresponding to each of the one or more distinctive constituent materials and the one or more iteratively labeled ambiguous constituent materials;

determine a similarity metric between the measured B0 field map and the simulated B0 field map during each iteration; and identify one or more constituent materials in each of the one or more dark regions based on the determined similarity metric to ascertain corresponding susceptibility value.

19. The system of claim 18, wherein the system is a magnetic resonance imaging system, a hybrid magnetic resonance-positron emission tomography system, a hybrid magnetic resonance-computed tomography system, a hybrid magnetic resonance-ultrasound system, or a hybrid magnetic resonance-x ray system.

* * * * *